United States Patent [19]

Hessel et al.

[11] Patent Number: 4,878,725
[45] Date of Patent: Nov. 7, 1989

[54] APPARATUS FOR THE CIRCUMFERENTIAL IRRADIATION OF OBJECTS

[75] Inventors: Stefan Hessel; Thomas Ischinger, both of Munich, Fed. Rep. of Germany

[73] Assignee: Messerschmitt-Bölkow-Blohm GmbH, Munich, Fed. Rep. of Germany

[21] Appl. No.: 198,453

[22] Filed: May 24, 1988

[30] Foreign Application Priority Data

May 25, 1987 [DE] Fed. Rep. of Germany ....... 3717525

[51] Int. Cl.[4] .............................................. G02B 6/32
[52] U.S. Cl. ..................................... 350/96.15; 128/6
[58] Field of Search ............... 350/96.10, 96.15, 96.18, 350/96.24–96.26; 128/4, 5, 6

[56] References Cited

U.S. PATENT DOCUMENTS

| 4,676,231 | 6/1987 | Hisazumi et al. | 128/6 |
| 4,681,093 | 7/1987 | Ono et al. | 128/6 |
| 4,693,556 | 9/1987 | McCaughan, Jr. | 350/96.15 X |
| 4,747,660 | 5/1988 | Nishioka et al. | 350/96.26 X |
| 4,760,840 | 8/1988 | Fournier, Jr. et al. | 128/6 X |
| 4,762,385 | 8/1988 | Fuse | 350/96.10 X |
| 4,784,133 | 11/1988 | Mackin | 128/6 X |
| 4,792,692 | 12/1988 | Herold et al. | 350/96.10 X |
| 4,795,430 | 1/1989 | Quinn et al. | 128/6 X |

Primary Examiner—William L. Sikes
Assistant Examiner—Akm E. Ullah
Attorney, Agent, or Firm—Kenyon & Kenyon

[57] ABSTRACT

For the circumferential irradiation of objects, especially of vessels, hollow organs and solid tissue, by optical radiation of high intensity which is conducted via a flexible optical fiber, the optical radiation is coupled into the optical fiber at a predetermined angle ($\beta_1, \beta_2$) to the surface normal of the end face of the optical fiber such that it leaves the distant end of the optical fiber in the form of a conical surface.

11 Claims, 3 Drawing Sheets

APPARATUS FOR THE CIRCUMFERENTIAL IRRADIATION OF OBJECTS

BACKGROUND OF THE INVENTION

The present invention relates to apparatus for the circumferential irradiation of objects, especially of vessels, hollow organs and solid tissue by means of high-intensity optical radiation which is conducted via a flexible optical fiber.

Such apparatus is in use in medical practice and is described, for instance, in "Laser in Surgery and Medicine" 6, pages 150–154 (1986) as well as in European Patent EP No. 01 52 766; high-intensity of the optical radiation is mentioned if the latter does not serve for illumination purposes but for coagulation or removal of tissue. In the first publication mentioned, the circumferential radiation of laser light is brought about by the provision that a cylindrical glass cap extending the fiber is placed inside out over the distant end; the inside wall of the latter is coated with a white synthetic material and its outside wall is roughened by sand blasting. By these measures, the greatest possible light scattering of the laser light emanating from the end of the fiber substantially axially is brought about, so that a diffuse radial radiation in the vicinity of the cap is accomplished. The apparatus described in the above-mentioned European Patent EP No. 01 52 766 differs, in contrast, in that the use of a cap is dispensed with and instead, the distant end of the optical fiber is freed of the jacketing. Also thereby, an essentially diffuse radial radiation of the laser light is to be achieved.

It is a disadvantage of the above-mentioned apparatus that the intensity is reduced substantially by the diffuse radiation, so that the coupled-in radiation power must be increased suitably for coagulation purposes or for removing tissue, stenoses and the like. This, however, also causes an increasing temperature rise of the cap and the distant end of the optical fiber. In addition, it is not possible with the known apparatus to bring, within a hollow organ with a diameter distinctly larger than that of the cap or the optical fiber, the laser radiation directed on small areas of the inside wall.

SUMMARY OF THE INVENTION

It is therefore an object of the present invention to provide apparatus for the circumferential irradiation of objects, ith which particularly laser light can be radiated oriented and with a higher intensity than heretofore.

The above and other objects of the invention are achieved by an apparatus for the circumferential irradiation of objects, especially of vessels, hollow organs and solid tissue by high-intensity optical radiation which is conducted via a flexible optical fiber, the optical radiation is coupled into the optical fiber at a predetermined angle ($\beta_1$, $\beta_2$) to the surface normal of the end face of the optical fiber in such a manner that it emanates at the distant end of the optical fiber in the form of a conical surface.

The invention makes use of the property of optical fibers known from "Handbook of Optics", Walter G. Driscoll, 1978, pages 13-7 to 13-8 namely, that a ray bundle not axially coupled emanates from the optical fiber in the form of a conical surface. While therefore the measures taken to date for the circumferential radiation of light conducted in an optical fiber relate exclusively to measures at the distant end of the optical fiber, the invention takes an approach not noted heretofore in that it couples the optical radiation at a predetermined aangle to the surface normal to the near end face of the optical fiber. The radiation emanating at the distant end of the optical fiber then has already a distinct radial component and even so remains oriented.

This radial component can now be increased further if a boundary surface of two transparent media with different index of refraction is provided around the distant end of the optical fiber, on which the radiation is incident at an angle, that means different from the normal direction. This can be realized in a simple manner by the provision that a cap similar to that one from "Laster in Surgery and Medicine" is slipped over the distant end which, however, comprises no measures for the diffuse scattering of the light but is as clear and transparent as possible. Depending on the application, care must then be taken that the media adjacent to the inside wall and the outside wall of the cap have different indices of refraction, which is brought about, for instance, by the provision that the hollowing spaace inside the cap is in contact with air and the outside wall of the cap either with the tissue to be irradiated, the tissue liquid or with a flushing liquid.

Due to the fact that the optical radiation emanates from the optical fiber oriented in spite of a radial component, the apparatus according to the invention can be arranged to particular according to the invention can be arranged to particular advantage in the central cavity of a balloon catheter which is closed at the distant end and is made, at least in the vicinity of the balloon, of a light-transparent material where the clearance of the catheter and the balloon can be filled with media of optically different density. This makes possible simultaneous balloon dilation and laser treatment, for instance, of a vessel wall. The optical fiber can be moved in the catheter system and thereby allows laser coagulation of the vessel wall in the vicinity of the balloon or on the entire length of the catheter. The tip of the balloon catheter-/optical fiber system at the distant end can be made conical and longer, to achieve thereby a modification of the refraction angle by diffraction at the boundary surface of the air and the balloon filling medium. The optical fiber can have at the distant end of the jacket an X-ray-impervious marking and, at a given distance therefrom, further to the near end, a marking, where this distance corresponds to the distance between the marking at the far end and the point of incidence of the radiation cone on the vessel wall which can be determined for the respective balloon diameter in the filled condition. Thereby, the treating physician can develop a good indication as to the distance from the distant end of the optical fiber, at which the conical surface of the optical radiation strikes the wall to be treated.

By mirror-coating the light-transparent cap on parts or its circumference, it becomes possible to treat the hollow organ to be treated or the like, not on the entire circumference with the optical radiation. Thereby, a selection of the area to be treated along the circumference can thereby be made.

Because the light-transparent cap has a mirror surface on parts of its circumference, it become possible to treat the hollow organ to be treated or the like with the optical radiation not on the entire circumference. Thereby, a selection of the region to be treated as to the circumference can thus be made.

If the cap is extended at the distant end by an X-ray-impervious wire tip, it become possible to use the optical fiber with the wired tip as a guide wire for a conventional balloon catheter system, as has not been possible heretofore. According to the present technology, one used to insert a guide wire into the blood vessel to be treated first, and then to introduce and remove the balloon catheter and the like along this guide wire without further threading problems. By adding a wire tip at the distant end of the optical fiber provided with a cap according to the invention, it is now possible to employ such optical fibers themselves as the guide wire for such applications. Since this wire tip is in addition impervious to X-rays, the great advantage is obtained that one can observe accurately on the X-ray screen where the distant end of the optical fiber is located.

If is further possible to provide the optical fiber on its jacket or also on the cap which may be extended up to the near end in a manner of a hose, with one or more X-ray-impervious markings so that the optical fiber can be observed on the X-ray screen without difficulty. These markings can either be individual marks or a continuous strip extending in the longitudinal direction of the optical fiber or the like.

Especially for treatment of arrhythmogenic structures in the heart muscle (myocard) it is a great advantage if the optical fiber has at the distant end or on the surface of the cap at least one electrode with which the effects of the coagulating radiation on the myocard can be measured directly.

BRIEF DESCRIPTION OF THE DRAWINGS

The invention will be described in greater detail in the following, referring to the embodiments partly shown schematically in the figures, where.

DETAILED DESCRIPTION

Figure 1:
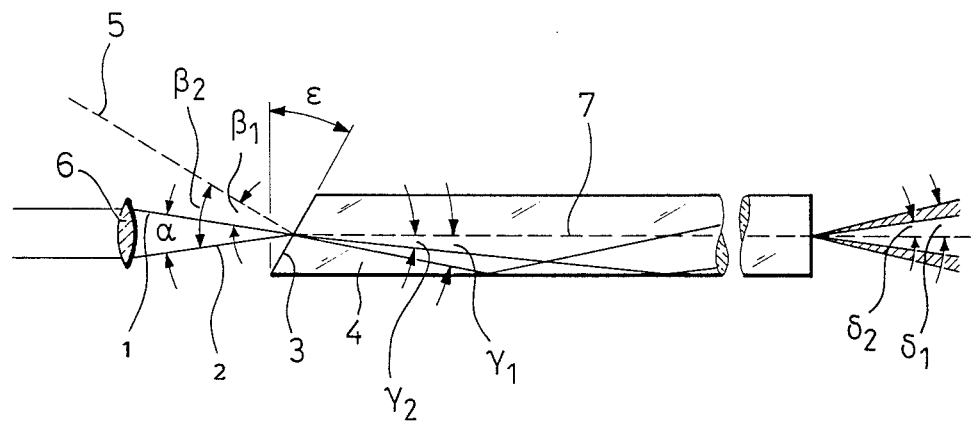
FIG. 1 shows the ray path within the optical fiber with oblique coupling.

For explaining the operation of the apparatus shown in FIG. 1, the following symbols will be used:

$\epsilon$ angle, at which the near end of the optical fiber is ground, $\alpha$ convergence angle by which laser radiation to be coupled is focused on the near end of the optical fiber, $\beta_1$ angle of the marginal ray 1 at the near end of the optical fiber relative to the surface normal of the end face of the optical fiber, $\beta_2$ angle of the marginal ray 2 (analogous to $\beta_1$), $\delta_1$ angle of the marginal ray 1 within the optical fiber relative to the longitudinal fiber axis, $\delta_2$ angle of the marginal ray 2 (analogous to $\alpha_1$), $\delta_{max}$ maximally permissible radiation angle within the optical fiber relative to the longitudinal fiber axis (condition for total reflection, $\delta_1$ exit angle of the marginal ray 1 at the distant end of the optical fiber relative to longitudinal fiber axis, $\delta_2$ exit angle of the marginal ray 2 (analogous to $\delta_1$), NA numerical aperture of the optical fiber and $n_L$ index of refraction of the core of the optical fiber.

Using the above-mentioned symbols, the following equations apply for the arrangement according to FIG. 1:

$$\gamma_{max} = \arcsin NA/n_L \quad (1)$$

$$\gamma_1 = \epsilon - \arcsin (1/n_L \times \sin \beta_1) \quad (2)$$

$$\gamma_2 = \epsilon - \arcsin (\gamma n_L \times \sin \beta_2) \quad (3)$$

$$\delta_1 = \arcsin (n_L \times \sin \gamma_1) \quad (4)$$

$$\delta_2 = \arcsin (n_L \times \sin \gamma_2) \quad (5)$$

With these equations, the radiation characteristic of the optical fiber and above all the aperture angle of the conical surface of the emanating radiation can be calculated. If the convergence angle $\alpha$ of the laser radiation to be coupled is small, the divergence of the amanating radiation within the conical surface, i.e., the differences between $\delta_1$ and $\delta_2$ can be neglected.

The radiation coming from a laser, not shown, is coupled-in via a lens 6 which focuses the radiation on the end face 3 of the optical fiber 4. The end face 3 is ground here at a certain angle $\epsilon$ so that the optical axis of the laser and the lens 6 can be located on the longitudinal axis 7 of the fiber and nevertheless an "oblique" coupling is achieved; this facilitates the mechanical design and the adjustment considerably as compared to such arrangements from "Handbood of Optics". The angle $\epsilon$ should be chosen as large as possible but must not exceed the condition applicable to the numerical aperture of the optical fiber according to Equation (1). The limit for the angle $\epsilon$ depends, according to Equations (2) and (3), on the convergence angle $\alpha$ and the index of refraction of the core of the optical fiber 4.

Figure 2:
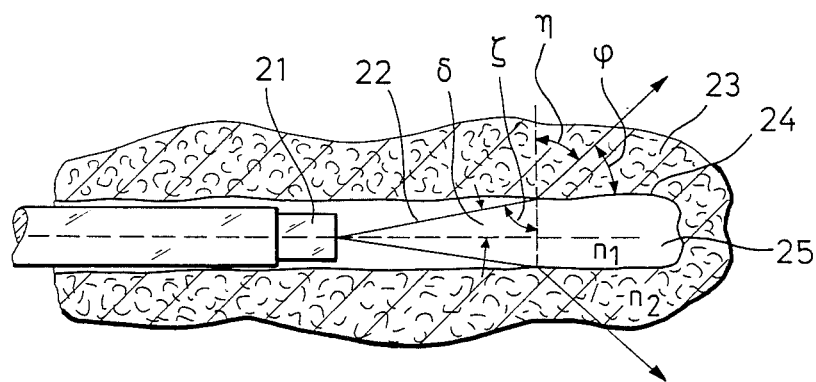
FIG. 2 shows the distant end of an optical fiber with measures for expanding the ray cone.

An increase of the aperture angle $\delta$ of the conical surface of the emanating radiation can be achieved according to FIG. 2, by the provision that the radiation 22 emanating from the optical fiber 21 strikes a cylindrical boundary surface 24, where the mediaa 23 and 25 outside and inside, respectively, of the cylindrical boundary surface 24 are transparent but with distinctly different indices of refraction; the medium 23 should have an index of refraction $n_2$ as large as possible, and the medium 25 an index of refraction $n_1$ as small as possible. For medical applications, the medium 25 can be air or an inert gas and the medium 23, water or salt solution therein. The radiation emanating from the optical fiber 21 in the form of a conical surface is then diffracted at this cylindrical boundary surface 24 in such a manner than an increase of the aperture angle $\delta$ of the conical surface is brought about. The following conditions apply:

$$\delta + \xi = 90° \quad (6)$$

$$\eta + \phi = 90° \quad (7)$$

$$\sin \zeta / \sin \eta = n_2/n_1 \quad (8)$$

$$V = \phi/\delta (\text{increase of the aperture angle}) \quad (9)$$

For a typical optical fiber used in medical technology in conjunction with neodymium/YAG lasers with a numerical aperture of NA=0.3 and an index of refraction of a fused silica core of n=1.45, a mean aperture angle $\delta=22°$ of the emanating radiation cone surface can be obtained by grinding the end face 3 at an angle $\epsilon=24°$. By arranging a coaxial cylindrical boundary surface 24 according to FIG. 2 with water for the medium 23 and the air for the medium 25, the aperture angle can be increased by about a factor of 4, so that the radiation takes place approximately at an angle of 43° relative to the fiber axis.

Figure 3:
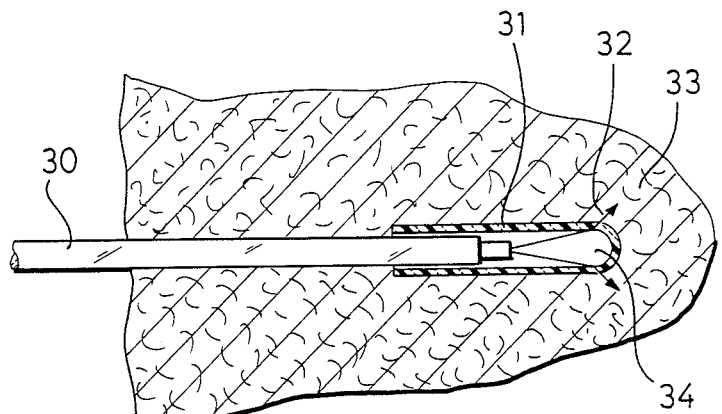
FIG. 3 shows an optical fiber with a cap for forming an optical boundary surface.

In the embodiment shown in FIG. 3, the distant end of the optical fiber 30 is surrounded by a transparent teflon cap 31 which encloses an air-filled cavity 34 with the fiber end. The distant end of the optical fiber 30 with the cap 31 is immersed deeply in the tissue 33 to be treated. The laser radiation 32 emanating from the optical fiber 30 in the form of a conical surface is diffracted here at the boundary surface air/tissue or tissue liquid in accordance with the optical properties; the optical properties of the teflon cap 31 need not be considered. With such an arrangement, for instance, deeply lodged arrhythmogenic structures in the myrocard can be coagulated.

Figure 4:
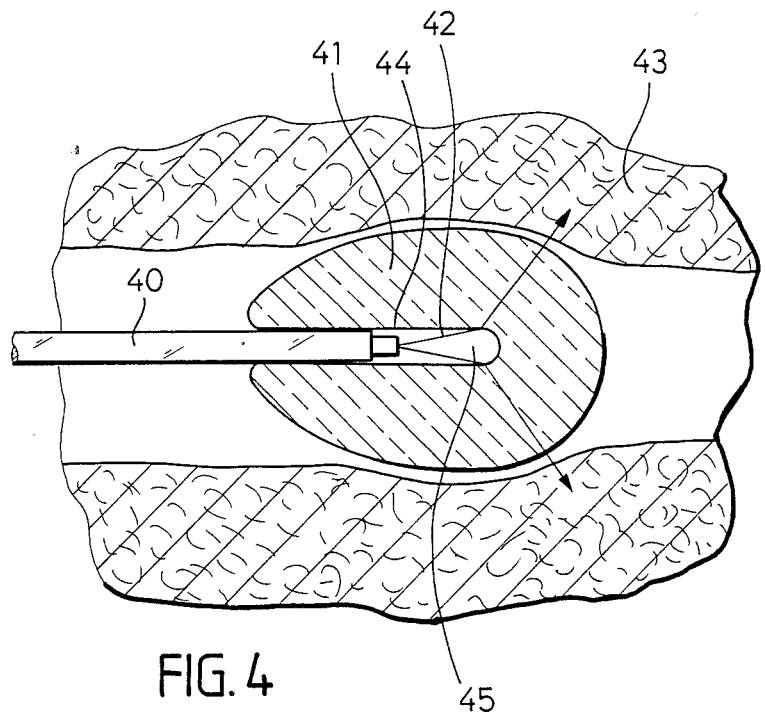
FIG. 4 shows an optical fiber with a drop-shaped glass cap.

In the embodiment shown in FIG. 4, a glass cap 41 with a drop of olive shape is arranged at the distant end which has an entrance hole 44 for the optical fiber 40. The distant end of the optical fiber 40 encloses with the hole 44 again an air-filled cavity 45 so that the laser radiation 42 leaving the optical fiber 40 is again diffracted at the wall of the hole 44 and thereby, the cone of radiation is enlarged further. With such a device, for instance, tumors 43 in the esophagus and in the bronchia can be coagulated.

Figure 5:
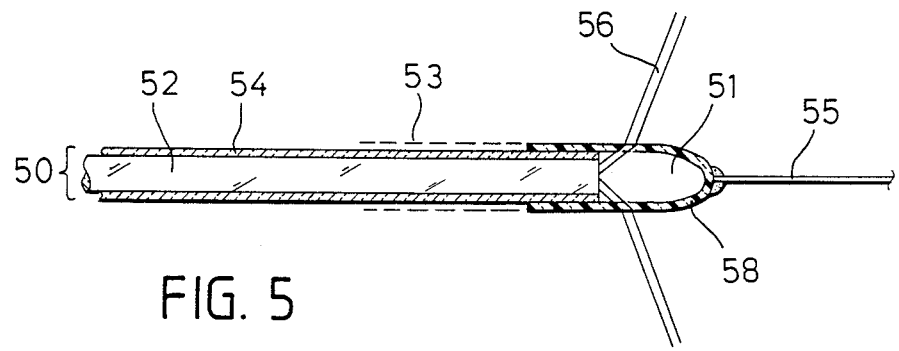
FIG. 5 shows an optical fiber with a cap and guide wire.

FIG. 5 shows the conventional fiber core 52 of a common optical fiber 50 with a jacket 54, where the laser light can be coupled into the fiber core in such a manner that it leaves the distant end in the form of a conical surface. By providing the optical fiber 50 with a cap 58 of light-transparent material which defines a cavity 51 which can be filled with a suitable gas, the cap 58 forms an optical boundary surface between the optically thinner medium in the cavity 51 and the optically denser medium around the outside of the optical fiber which has been filled, for instance, into the hollow organ to be treated. Such an optically denser medium can be without problem an X-ray-impervious light transparent liquid. By designing the optical fiber in this manner with a cap 58 defining the optical boundary surface, the conical surface is enlarged as in FIG. 4 relatively with the consequence that the laser light 56 strikes the wall to be treated or the like largely as far as possible.

The cap 58 can be extended in the manner of a hose up to the near end of the optical fiber 50 (53) and can be flushed or cooled with compressed gas, for instance, on the inside.

In a particularly advantageous manner, the cap 58 is provided at its front end with a wire tip 55 which is made sufficiently long to use the optical fiber itself as a guide wire, for instance, for a conventional balloon catheter system, in which the balloon catheter is pushed over a guide wire after the latter has been placed in the vessel or organ to be examined.

Figure 6:
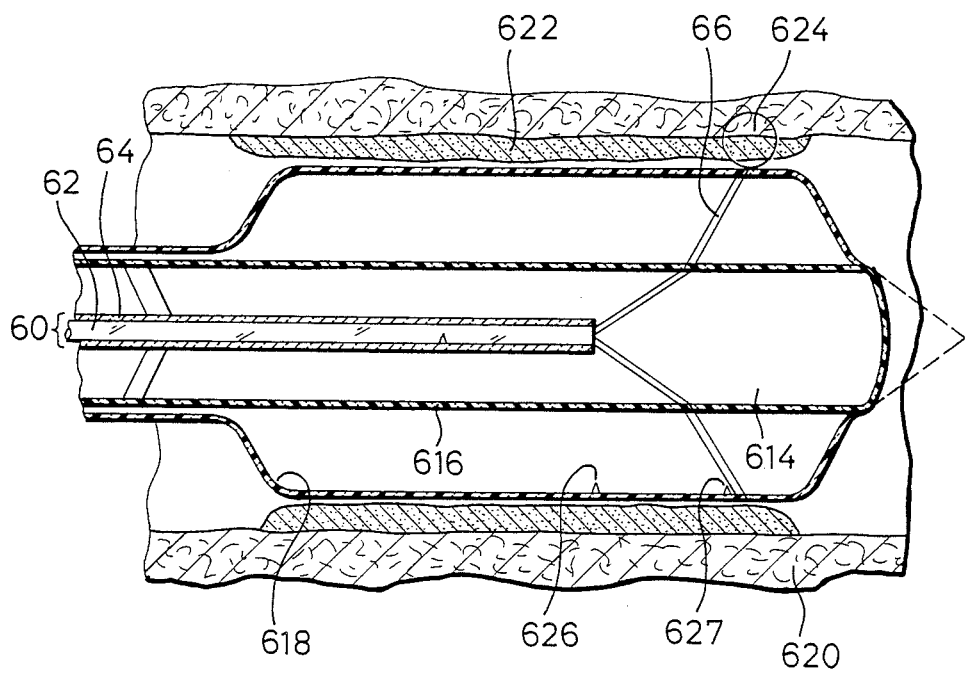
FIG. 6 shows an optical fiber which is inserted into a balloon catheter, where the optical boundary surface is formed by the inside wall of the balloon catheter.

In FIG. 6, the optical fiber is shown in conjunction with a balloon catheter when inserted into a vessel wall, in which deposits 622 on the inside of the vessel wall 620 are dilated by the balloon 618 of the balloon catheter 616. In the region 624, laser coagulation takes place, specifically by the conical laser light surface 66 which is expanded in accordance with the invention and leaves the fiber core 62 of the optical fiber 60. The latter is arranged in the center clearance 614 of the balloon catheter 616 which is closed at the distant end, either as shown with a more or less smooth wall, or by means of a finely tapered wall, whereby an optical boundary surface is created which no longer extends coaxially to the longitudinal axis of the catheter. The central clearance 614 of the balloon catheter must be filled with a medium which is optically thinner than the medium in the balloon 618 of the balloon catheter in order to achieve the desired spreading out of the conical laser-like surface. The balloon 618 has two X-ray impervious markings 626 and 627 which are provided, for one, at the height of the distant end of the optical fiber, and otherwise, at the angular striking area of the radiation cone 66 on the wall of the balloon. By the combination, shown in FIG. 6, of a laterally radiating optical fiber with a balloon catheter, it is achieved that dilation and coagulation can be performed simultaneously. This has not been possible heretofore.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. Apparatus for the circumferential irradiation of objects, especially of vessels, hollow organs and solid tissue by high-intensity optical radiation which is conducted to the irradiation site by a flexible optical fiber having a near end and a distant end, wherein the optical radiation comprises two marginal rays in a cross section defining an illuminated line, the radiation being coupled into an end face of the near end of the optical fiber at a predetermined angle ($\beta_1$, $\beta_2$) to the surface normal of the end face of the optical fiber such that the optical radiation emanates at the distant end of the optical fiber in the form of a conical surface, said predetermined angle $\beta_1$ comprising the angle of a first of said marginal rays with respect to the surface normal and said predetermined angle $\beta_2$ comprising the angle of a second of said marginal rays with respect to the surface normal, said predetermined angles $\beta_1$ and $\beta_2$ each being greater than 0°.

2. The apparatus recited in claim 1, wherein the end face at the near end of the optical fiber is ground at an angle ($\epsilon$) from the fiber axis, and the coupling of the optical radiation takes place in the direction of the fiber axis.

3. The apparatus recited in claim 1 where the emaanating radiation has an aperture angle ($\delta$) and for increasing the aperture angle of the emanating radiation cone surface, means are provided for generating around the distant end of the optical fiber a boundary surface of two transparent media with different coefficients of refraction ($n_2$, $n_1$) which the conical radiation surface strikes at an angle.

4. The apparatus recited in claim 1, wherein the distant end of the optical fiber comprises a substantially cylindrical cap with a transparent cylinder wall, a hollow space being provided between the cap and the end face of the distant end of the optical fiber.

5. The apparatus recited in claim 4, wherein the hollow space is filled with a gaseous medium.

6. The apparatus recited in claim 4, wherein the cap is extended by a hose up to the near end of the optical fiber.

7. The apparatus recited in claim 1, wherein the distant end of the optical fiber is arranged in a central cavity of a balloon catheter closed at the distance end which catheter comprises, in the vicinity of the balloon, a transparent material, and wherein the central cavity of the catheter and a cavity of the balloon are filled with transparent media of optically different density.

8. The apparatus recited in claim 4, wherein the cap has a mirror surface on a part of its circumference.

9. The apparatus recited in claim 4, wherein the cap is extended at the distant end by a wire tip impervious to X-rays.

10. The apparatus recited in claim 4, wherein at least one X-ray impervious marking is provided on the cap.

11. The appratus recited in claim 7, wherein at least one X-ray impervious marking is provided on the balloon catheter.

* * * * *

UNITED STATES PATENT AND TRADEMARK OFFICE
CERTIFICATE OF CORRECTION

PATENT NO. : 4,878,725

DATED : November 7, 1989

INVENTOR(S) : Stefan Hessel et al

It is certified that error appears in the above-identified patent and that said Letters Patent is hereby corrected as shown below:

In Column 1, line 48, change "...ith which particularly..." to read --...with which particularly...--

Column 2, line 3, change "aangle to the surface normal to the near end face..." to read
--angle to the surface normal of the near end face-- lines 13-14, change "...similar to that one from "Laster in Surgery and Medicine" to read
--...similar to the one from "Laser in Surgery and Medicine"

line 21, change "...hollowing spaace..." to read --...hollow space...-- delete line 29

Column 3, lines 61, 63 and 64, change "$\hat{\delta}_1$ angle" "$\hat{\delta}_2$ angle" and "$\hat{\delta}_{max}$" repsectively to read
--$\hat{\gamma}_1$ angle--; --$\hat{\gamma}_2$ angle--; --$\hat{\gamma}_{max}$--

UNITED STATES PATENT AND TRADEMARK OFFICE
CERTIFICATE OF CORRECTION

PATENT NO. : 4,878,725

DATED : November 7, 1989

INVENTOR(S) : Stefan Hessel et al

It is certified that error appears in the above-identified patent and that said Letters Patent is hereby corrected as shown below:

Column 4, line 11, should read $$--\gamma_2 = \varepsilon - \arcsin(1/n_L \times \sin\beta_2) --$$

line 21, change "amanating" to read --emanating--

Column 5, line 24, change "with a drop of olive" to read --with a drop or olive--

Column 7, line 10, change "the distance end" to read --the distant end--

Signed and Sealed this

Fifth Day of November, 1991

*Attest:*

HARRY F. MANBECK, JR.

*Attesting Officer*     *Commissioner of Patents and Trademarks*